US00PP18971P3

(12) United States Plant Patent
Nielsen

(10) Patent No.: US PP18,971 P3
(45) Date of Patent: Jun. 24, 2008

(54) *DAHLIA* PLANT NAMED 'DATRETTEN'

(50) Latin Name: ***Dahlia* sp.**
Varietal Denomination: DATRETTEN

(75) Inventor: Rune Harboe Nielsen, Odense (DK)

(73) Assignee: Dalina APS, Odense N (DK)

( * ) Notice: Subject to any disclaimer, the term of this patent is extended or adjusted under 35 U.S.C. 154(b) by 0 days.

(21) Appl. No.: 11/707,506

(22) Filed: Feb. 16, 2007

(65) Prior Publication Data

US 2007/0199121 P1 Aug. 23, 2007

(30) Foreign Application Priority Data

Feb. 21, 2006 (QZ) ..... 2006/0527

(51) Int. Cl.
*A01H 5/00* (2006.01)

(52) U.S. Cl. ..... Plt./321
(58) Field of Classification Search ..... Plt./321
See application file for complete search history.

(56) References Cited

PUBLICATIONS

EU–CPVO Application Form with Technical Questionnaire and Proposal for Variety Denomination for corresponding, international PBR application, CPVO 2006/0527 filed Feb. 21, 2006. (13 pages).
Print–out of the Canadian Food Inspection Agency Plant Varieties Journal for Oct. 2006, No. 61, confirming the filing date and application No. for corresponding Canadian PBR application No. 06/5487 filed on Jun. 1, 2006 (2 pages).

*Primary Examiner*—Annette H Para
(74) *Attorney, Agent, or Firm*—Foley & Lardner LLP

(57) ABSTRACT

A new and distinct cultivar of *Dahlia* plant named 'Datretten' characterized by its ray floret color (when opening, upper side): base: red, RHS 44B and apex: white, RHS N155B; capitulum (composite flower head): 9.5 to 10.5 cm in diameter, with a large number of ray florets (about 100 to 140); mature leaves about 8 to 12 cm in length, mostly compound, with 1-5 leaflets, and immature leaves about 4 to 6 cm in length, compound, with 1-5 leaflets; and vigorous plant vigor, growing upright with slight spread to form cylindrical-shaped plant.

4 Drawing Sheets

Latin name of the genus and species of the claimed plant: *Dahlia* sp.
Variety denomination: 'Datretten'.

BACKGROUND OF THE INVENTION

The present invention relates to a new and distinct cultivar of *Dahlia* plant, botanically known as *Dahlia* sp. of the Compositae (Asteraceae) family, hereinafter referred to by the cultivar name 'Datretten'.

The new *Dahlia* cultivar is a product of a planned breeding program conducted by the inventor, Rune Harboe Nielsen, in Odense, Denmark. The objective of the breeding program is to develop a new *Dahlia* variety with a compact, strong and healthy growth habit, suitable for large scale container production; fully double flowering creating a globular-shaped flower head (composite flower head with many ray florets); and flower heads with new, vibrant colors.

The new *Dahlia* cultivar originated from a cross made in a controlled breeding program by the inventor in 2003, in Fyn, Odense, Denmark. The female or seed parent is a *Dahlia* cultivar designated '01.149L' (unpatented). The male or pollen parent is a *Dahlia* cultivar designated 'Daseks' (unpatented in the US, granted as EU-CPVO application number 19981438). The new *Dahlia* 'Datretten' was discovered and selected by the inventor as a single flowering plant within the progeny of the stated cross in May of 2004 in a controlled environment in Odense, Denmark.

Asexual reproduction of the new *Dahlia* cultivar by vegetative cuttings was first performed in August of 2004 in Odense, Denmark, and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'Datretten', which in combination distinguish this *Dahlia* as a new and distinct cultivar:

1. Ray floret color (when opening, upper side): Base: Red, RHS 44B; Apex: White, RHS N155B;
2. Capitulum (composite flower head): 9.5 to 10.5 cm in diameter, with a large number of ray florets (about 100 to 140);
3. Foliage: Mature leaves are about 8 to 12 cm in length, mostly compound, with 1-5 leaflets and immature leaves are about 4 to 6 cm in length, compound, with 1-5 leaflets; and
4. Plant Vigor and Growth Habit: Vigorous, grows upright with slight spread to form cylindrical-shaped plant.

Plants of the new *Dahlia* 'Datretten' differ from plants of the male parent 'Daseks' (unpatented in the US, granted as EU-CPVO application number 19981438) in the characteristics described in Table 1. Plants of the female parent '01.200A' (unpatented) are unavailable for comparison to plants of 'Datretten'.

TABLE 1

| Characteristic | New Cultivar 'DATRETTEN' | Male Parent 'DASEKS' (unpatented in US, granted as EU-CPVO 19981438) |
|---|---|---|
| Color of Ray Floret (when opening, upper side): | Bi-color Base: red, RHS 44B; Apex: white, RHS N155B. | Red-purple, RHS 60A |
| Capitulum Diameter: | 9.5 to 10.5 mm | 50 to 70 mm |
| Foliage: | Mostly compound, with 1-5 leaflets | Single leaves. |
| Growth Habit: | Grows upright with slight spread to form cylindrical-shaped plant | Grows erect to semi-erect in compact plant shape. |

Of the many commercial cultivars known to the present inventor, the most similar in comparison to the new *Dahlia* 'Datretten' is the *Dahlia* 'Papagaya' (unpatented in the US, granted as EU-CPVO application number 20031209), in the characteristics described in Table 2:

TABLE 2

| Characteristic | New Cultivar 'DATRETTEN' | Comparison Cultivar 'PAPAGAYA' (granted as EU-CPVO application number 20031209) |
|---|---|---|
| Color of Ray Floret (when opening, upper side): | Bi-color Base: red, RHS 44B; Apex: white, RHS N155B. | Bi-color Base: Red, 46B. Apex: White, RHS 155B. |
| Number of Ray Florets. | About 100 to 140 | About 40 to 90 |
| Capitulum Diameter: | 9.5 to 10.5 mm | 8 to 9 cm |
| Foliage: | Mostly compound, with 1-5 leaflets | Mostly single, few compound, tri-lobed. |
| Plant Vigor and Growth Habit: | Vigorous, grows upright with slight spread to form cylindrical-shaped plant. | Vigorous, grows upright and spreading to form globular-shaped plant. |
| Plant Height: | About 40 to 45 cm | About 30 to 35 cm |

BRIEF DESCRIPTION OF THE PHOTOGRAPHS

The accompanying photographs illustrate the overall appearance of the new *Dahlia* 'Datretten' showing the colors as true as is reasonably possible with colored reproductions of this type. Colors in the photographs may differ slightly from the color value cited in the detailed botanical description which accurately describe the colors of 'Datretten'.

DETAILED BOTANICAL DESCRIPTION

Figure 1:
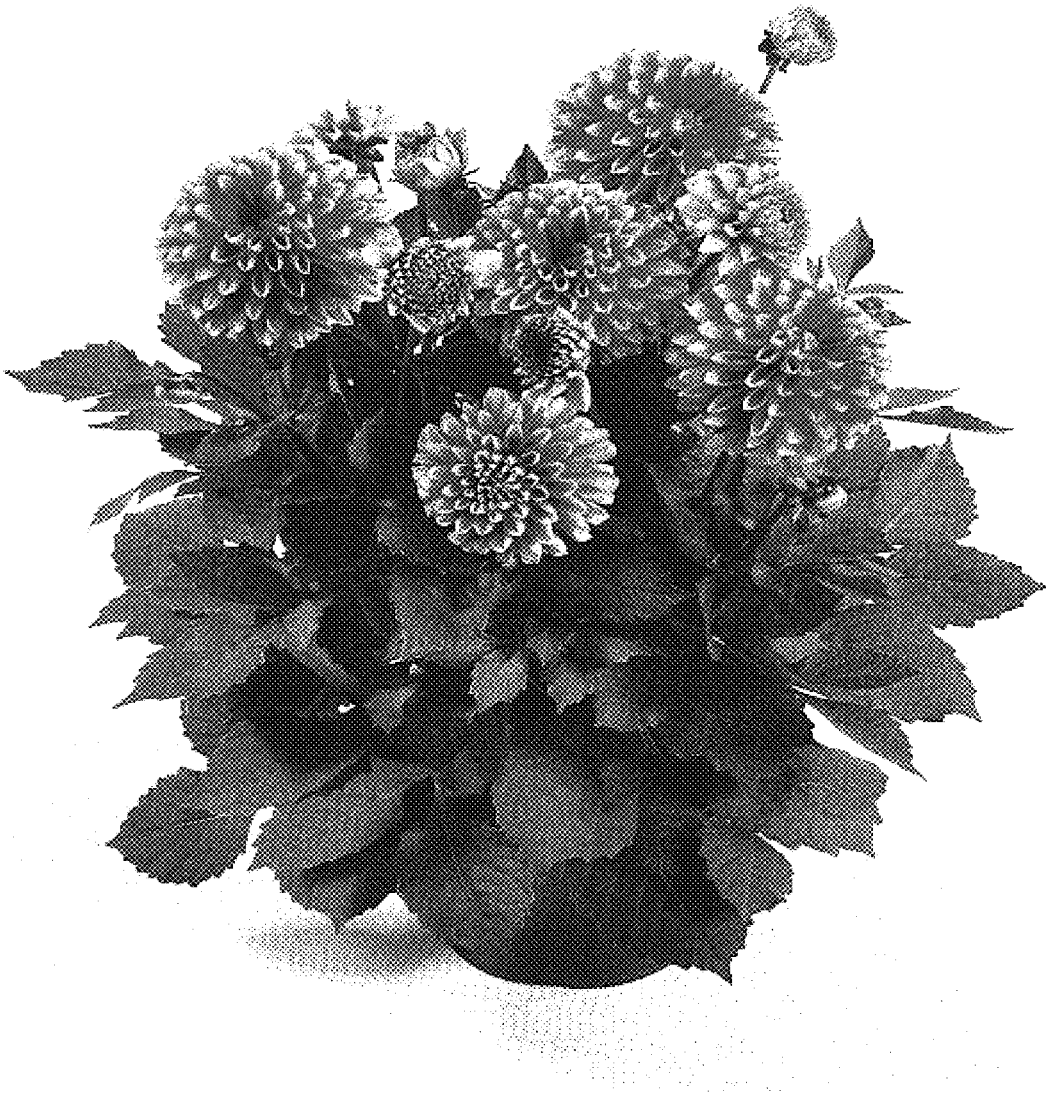
FIG. 1 shows a side view perspective of a typical flowering plant of 'Datretten' in a 15 cm pot (volume 2 liters), at 9 weeks of age after potting.
Figure 2:
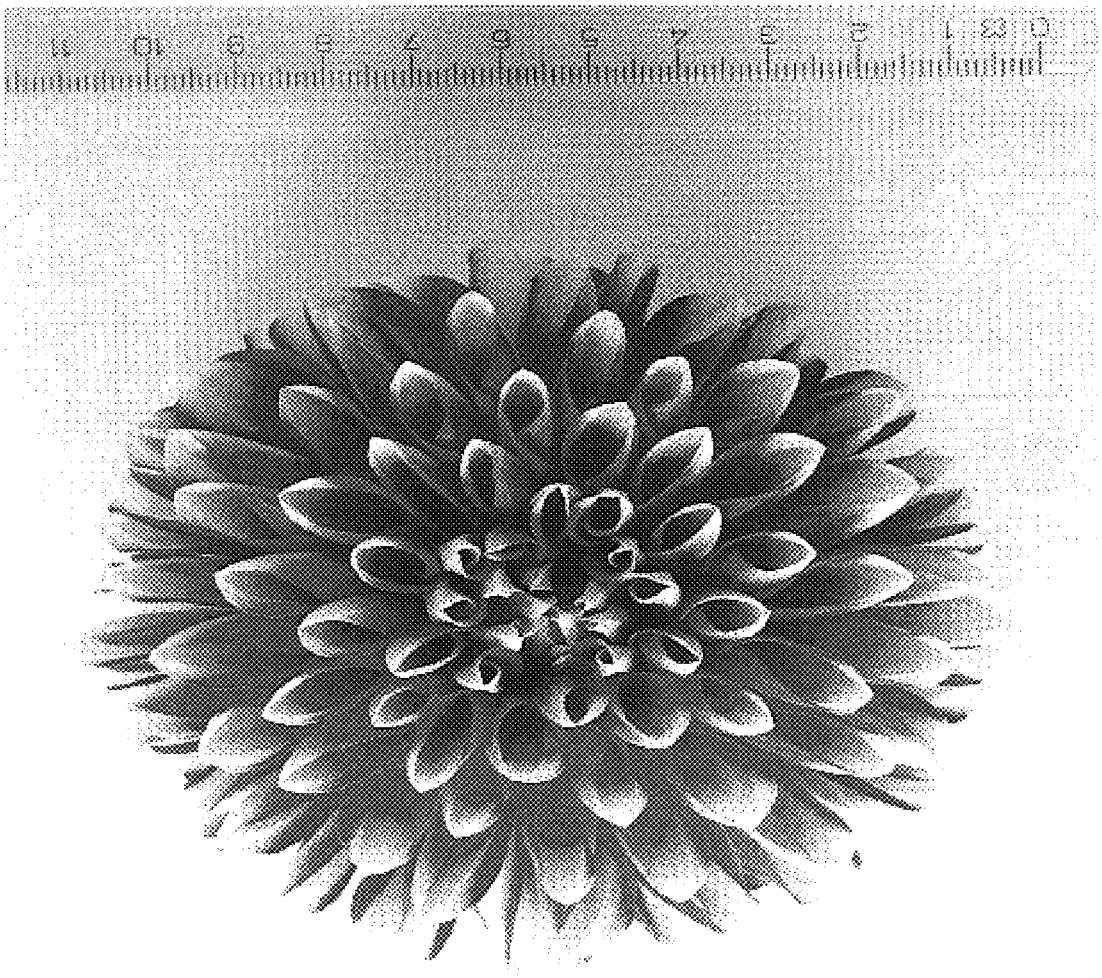
FIG. 2 shows a top view perspective of a fully opened capitulum of 'Datretten' (as identified by breeder reference 03.217E), at 9 weeks of age after potting.
Figure 3:
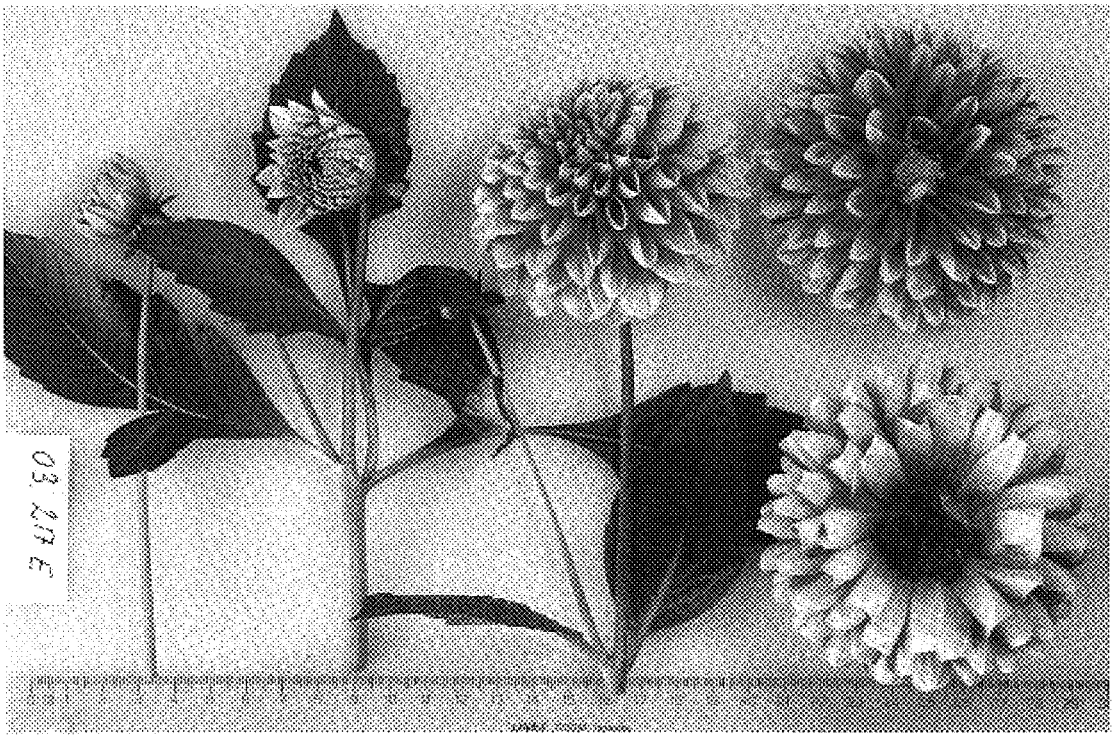
FIG. 3 shows a close-up view of the typical capitulum of 'Datretten' (as identified by breeder reference 03.217E) in different stages of development.
Figure 4:
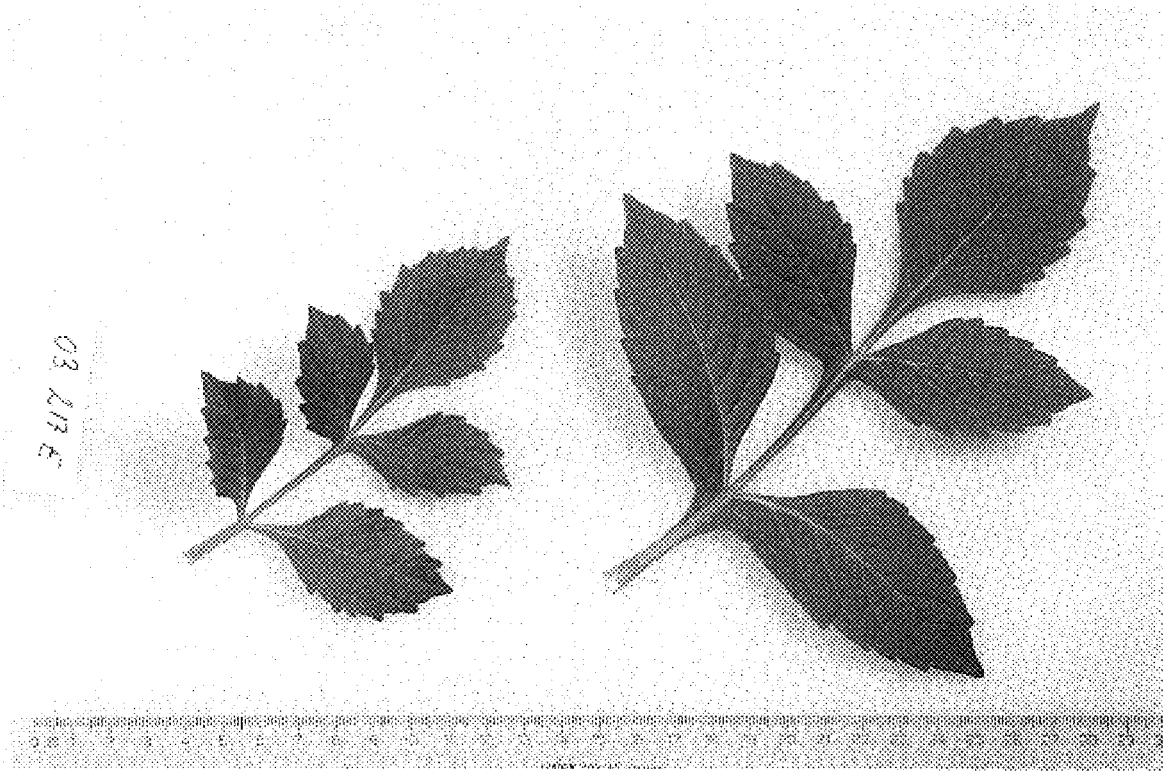
FIG. 4 shows a close-up top view of the typical foliage of 'Datretten' (as identified by breeder reference 03.217E), at 9 weeks of age after potting.

The new *Dahlia* 'Datretten' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe the new *Dahlia* 'Datretten' as grown in a protected environment in a glass, greenhouse in Fyn, Odense, Denmark, under conditions which closely approximate those generally used in commercial practice. During propagation, conducted in a glass, greenhouse, vegetative cuttings were planted in small propagation pots with peat as substrate, and then placed in a plastic tunnel averaging about 21° C. and received photoperiodic treatments of 18 hours. Supplementary light was given when natural light fell below 3000-4000 Lux. Rooting occurred about 12 days after planting. In third week after planting, young plants were potted in an 11 cm pot in a glass, greenhouse maintained at 18° C. to 22° C. during the day, and at 17° C. to 19° C. during the night. Photoperiodic treatments were continued at 18 hours, and supplementary light was given when natural light fell below 3000-4000 Lux. Irrigation was done with water. The EC measured in the soil was maintained between 2.0 to 3.0. One week after potting, the first growth regulation was given: a spray with 85% daminozide, 0.2%, 25 ml/m$^2$. During the production time, 4 additional sprayings were given with 85% daminozide, 0.2%, 70-100 ml/m$^2$.

Color references are made to The Royal Horticultural Society Colour Chart (R.H.S.), 2001 edition, except where general colors of ordinary significance are used. Color values were taken under daylight conditions between approximately 12:00 PM and 2:00 PM in Fyn, Odense, Denmark. The age of the 'Datretten' plants described is 12 weeks (including propagation time).

Classification:

*Botanical.*—*Dahlia* sp.

Parentage:

*Female or seed parent.*—*Dahlia* cultivar designated '01.149L' (unpatented).

*Male or pollen parent.*—*Dahlia* cultivar designated 'Daseks' (unpatented in US, granted as EU-CPVO application number 19981438).

Propagation:

*Type.*—Vegetative cuttings.

*Rooting description.*—Fibrous and freely-branching.

*Height of rooting structure.*—Depends on container, can grow to about 30 to 40 cm.

*Diameter of rooting structure.*—Depends on container, can grow to about 30 to 40 cm.

*Color of roots.*—White, RHS 155B.

*Time to initiate roots.*—About 12 days at 21° C.

*Time to produce a rooted cutting.*—About 21 days at 21° C. during rooting phase, followed by 18° C.

*Tubers.*—Will form under short day conditions, 12 hours of darkness. Tubers may develop in late summer/early autumn when planted outdoors.

Plant:

*Crop time.*—After rooting, about 9 to 10 weeks are required to produce finished flowering plants in 15 cm pots.

*Plant vigor.*—Vigorous.

*Form.*—Cylindrical, grows upright with slight spread.

*Size.*—Height (from soil level to top of plant plane): About 40 to 45 cm. Height (from soil level to top of foliage): About 25 to 35 cm. Spread: About 40 to 45 cm.

*Stem.*—Appearance/Shape: Circular, hollow, glabrous, ridged. Diameter: About 8 to 12 cm. Aspect: Upright to outward. Strength: Strong. Texture: Glaucous. Pubescence: None. Color: Main color: Yellow-green, RHS 144A. Apical parts: Grey-brown, RHS 199A.

*Lateral branches.*—Quantity per plant: About 6 to 7 (when pinching over 3 pair of leaves). Length: (including inflorescences): About 25 to 40 cm. (from break to base of peduncle); About 12 to 15 cm. Diameter: About 8 to 12 mm. Color: Main color: Yellow-green, RHS 144A. Apical parts: Grey-brown, RHS 199A. Habit: Freely branching. Basal Branching: Yes. Pinching: Pinching recommended. Internode length: About 3 to 8 cm.

Foliage:

*Type.*—First 2 to 3 pairs on basic lateral branch are single. Thereafter, compound with about 3 to 5 leaflets.

*Quantity of leaves per lateral branch.*—About 4 to 10.

*Quantity of leaflets per compound leaf.*—About 1 to 5.

*Color (leaves and leaflets).*—Color (mature): Upper side: Green, RHS 139A. Under side: Greyed-green, RHS 191B. Color (immature): Upper side: Green, RHS 139A. Under side: Greyed-green, RHS 191A.

*Venation (leaves and leaflets).*—Pattern: Pinnate. Color: Upper side: Yellow-green, RHS 146A. Under side: Yellow-green, RHS 146A.

*Simple leaves.*—Arrangement: Opposite, decussate. Length: Mature leaves (at base): 8 to 12 cm. Immature leaves: 4 to 6 cm. Width: Mature leaves: 4-7 cm. Immature leaves: 3-6 cm. Shape: Ovate to cordate, cuspidate tip, rounded base. Margin: Crenate. Texture (both sides): Rugose. Petiole: Shape: Semi circular. Length: About 2 to 7 cm. Diameter: About 3 to 6 mm. Color: Upper side: Brown, RHS 200B. Under side: Yellow-green, RHS 146A.

*Compound leaves.*—Arrangement and shape: Compound with 3-5 leaflets. Leaves near the petiole are often tri-lobed or single. Length: Up to 25 cm, generally about 15 cm. Width: Up to 22 cm, generally about 14 cm. Shape: Elliptical, acuminate tip, decurrent base. Margin: Dentate. Texture (both sides): Rugose. Petiole: Shape: Semi circular. Length: About 2 to 5 cm. Diameter: About 3 to 6 mm. Color: Upper side: Brown, RHS 200B. Under side: Yellow-green, RHS 146A. Leaflets of Compound Leaf: Terminal: Quantity: One. Length: About 5 to 9 cm. Width: About 3 to 4 cm. Rachis: Length: About 3 to 5 cm. Diameter: About 2 to 5 mm. Color: Yellow-green, RHS 146A. Lateral: Quantity: About 2 to 4. Length: About 4 to 9 cm. Width: About 2 to 5 cm.

Flowering description:

*Natural flowering season.*—Grown outside as a bedding plant, flowering occurs continuously during growing season (In Denmark, from June to beginning of October). Plants can be brought to flower anytime when grown under the recommended greenhouse conditions.

*Time to first flower.*—About 8 to 9 weeks from potting of a rooted cutting.

*Lastingness of individual blooms on plant.*—Depending on weather conditions, about 7 to 12 days.

*Fragrance.*—None.

Inflorescence description:

*Type.*—Capitulum (composite flower head).

*Arrangement.*—Persistent, single, composite inflorescences from leaf axils. Disc and ray florets arranged acropetally on a capitulum.

*Flowering aspect.*—Upright, slightly spreading. Young flower head/buds initially 70° to 90° turning to 30° when flower head opens.

*Quantity of flowers and buds per lateral branch.*—About 1 open capitulum and 3 buds.

*Fragrance.*—None.

*Bud.*—Quantity: About 3 to 5 per lateral stem (buds continue to develop when the dead composite flower heads are removed). Rate of Opening: About 4 to 10 days for bud to progress from first color to fully opened capitulum, depending on temperature and light conditions. Shape: Globular. Length (when color shows): About 1.5 to 2.0 cm. Diameter (when color shows): About 2.5 to 3.0 cm. Texture: Glabrous, shining. Color: Yellow-green, RHS 144B.

*Peduncle.*—Length: About 10 to 18 cm. Diameter: About 4 to 6 cm. Strength: Strong. Aspect (angle to vertical): First flower: About 0° to 10°; Second flower: About 20° to 30°. Color: Green, RHS 138B, with stripes of brown, RHS 200C.

*Inflorescence.*—Inflorescence depth (height): About 6 to 7 cm. Inflorescence diameter: About 9.5 to 10.5 cm. Disc diameter: About 1.4 cm. Receptacle diameter: About 1.6 cm. Receptacle height: About 0.9 cm.

*Ray florets.*—Arrangement: Imbricate, in about 7-9 whorls of ray florets, each with 10 to 18 florets to equal a total of about 100-140 ray florets per capitulum, depending on light and temperature conditions. Appearance: Obovate. Overall shape: Circular to elliptic, involute with a rounded tip. Apex shape: Obtuse. Base shape: Acuminate, fused to form tube. Length: About 35 to 45 mm. Diameter (width): About 2 to 30 mm. Margin: Entire. Texture: Upper side: Glabrous, smooth. Under side: Glabrous with visible veins. Orientation: Initially 15° from vertical, with development, to 160° from vertical. Color: Development and tones of color for florets may change slightly depending on light and temperature conditions. When opening: Upper side: Primarily red, RHS 44B, with white tip, RHS N155B. When fully opened: Upper side: Primarily red, RHS 45B, with white tip, RHS N155B.

*Disc florets.*—Arrangement: Massed at center of capitulum, about 40-90 disc florets per capitulum, which are yellow-white in color at the lower half, but appear more yellow in appearance due to the transparent corollas and the underlying yellow color from the anthers. Appearance: Tubular to single, fused corolla. Overall shape: Tubular. Apex shape: Star with 5 triangular tips. Base shape: Fused to tube. Length: About 4 to 6 mm. Diameter: About 1 mm. Margin: Entire. Texture (both surfaces): Glabrous. Color: Transparent, yellow-white, RHS 158C, letting the yellow, RHS 13A color of the anthers come through (before anthesis), to yellow-orange, RHS 20A (at anthesis).

*Phyllaries.*—Quantity: One subtending each floret. About 140 to 200 phyllaries per capitulum. Appearance and arrangement: Thin, translucent, papery. Phyllaries, arranged acropetally on the capitulum. Overall shape: Subulate. Apex shape: Acute with rounded tip. Base shape: Fused. Length: About 10 to 14 mm. Width: About 5 to 8 mm. Margin: Entire. Texture (both sides): Glabrous. Color: Mature: Yellow-green, RHS 151D, to green, RHS 139D, at base. Immature: Yellow-green, RHS 151D, to green, RHS 139D, at base.

*Bracts.*—Quantity: About 5 to 8. Appearance and arrangement: Reflexed, involucral bracts. Overall shape: Subovate. Apex shape: Acute to rounded. Base shape: Sessile. Length: About 10 to 14 mm. Width: About 6 to 8 mm. Margin: Entire. Texture (both sides): Glabrous. Color: Mature: Upper side: Green, RHS 139A. Under side: Green, RHS 139B. Immature: Upper side: Green, RHS 139A. Under side: Green, RHS 138B.

Reproductive organs:

*Androecium.*—Stamen: Number: 5, fused into synandrous tube around style. Disc florets fertile, ray florets sterile. Length: About 10 to 12 mm. Anther: Shape: Tubular. Length: About 4 to 5 mm. Color: Yellow-orange, RHS 20A. Pollen: Amount: Abundant. Color: Yellow-orange, RHS 20A.

*Gynoecium.*—Pistil: Quantity: One. Length: About 8-10 mm. Stigma: Shape: Bifurcate. Length: About 4-8 mm. Color: Yellow-orange, RHS 20A. Style: Length: About 6-8 mm. Color: Yellow-orange, RHS 20D. Ovary: Diameter: About 1 mm. Color: Yellow-green 151C.

Seed/fruit: None observed.

Disease/pest resistance: Resistance to pathogens and pests common to *Dahlia* have not been observed.

Disease/pest susceptibility: Susceptibility to pathogens and pests common to *Dahlia* have not been observed.

Temperature tolerance: Tolerant to a low temperature of about 2° C. (but flowering ceases at constant temperature of 12° C.) and tolerant to a high temperature of about 35° C. High temperatures might reduce flowering.

Growth regulators: Daminozide (85% water soluble dry concentrate formulation).

I claim:

1. A new and distinct cultivar of *Dahlia* plant named 'Datretten', as described and illustrated herein.

* * * * *

03217E